(12) United States Patent
Carralero et al.

(10) Patent No.: US 9,772,539 B2
(45) Date of Patent: Sep. 26, 2017

(54) OPTICAL SENSOR AND METHOD OF MANUFACTURE

(71) Applicant: THE BOEING COMPANY, Huntington Beach, CA (US)

(72) Inventors: Michael A. Carralero, Huntington Beach, CA (US); Ty A. Larsen, Everett, WA (US)

(73) Assignee: THE BOEING COMPANY, Chicago, IL (US)

( * ) Notice: Subject to any disclaimer, the term of this patent is extended or adjusted under 35 U.S.C. 154(b) by 0 days.

(21) Appl. No.: 14/819,545

(22) Filed: Aug. 6, 2015

(65) Prior Publication Data

US 2016/0085134 A1 Mar. 24, 2016

Related U.S. Application Data

(62) Division of application No. 12/589,668, filed on Oct. 26, 2009, now Pat. No. 9,482,927.

(51) Int. Cl.
| | |
|---|---|
| *G02F 1/29* | (2006.01) |
| *G02F 1/295* | (2006.01) |
| *A61B 5/00* | (2006.01) |
| *G01N 21/55* | (2014.01) |
| *G01D 5/26* | (2006.01) |
| *G01N 21/47* | (2006.01) |
| *G01B 9/02* | (2006.01) |
| *G02B 6/122* | (2006.01) |

(52) U.S. Cl.
CPC ............ *G02F 1/295* (2013.01); *A61B 5/0066* (2013.01); *G01D 5/268* (2013.01); *G01N 21/55* (2013.01); *A61B 5/0059* (2013.01); *G01B 9/02091* (2013.01); *G01B 2290/45* (2013.01); *G01N 21/4795* (2013.01); *G01N 2201/068* (2013.01); *G01N 2201/088* (2013.01); *G02B 6/1225* (2013.01)

(58) Field of Classification Search
CPC ................ G02B 1/005; G02B 19/0023; G02B 19/0047; G02B 26/10; G02B 27/0093; G02B 6/1225; G02B 6/0065
See application file for complete search history.

(56) References Cited

U.S. PATENT DOCUMENTS

| | | | |
|---|---|---|---|
| 4,492,121 | A | 1/1985 | Lehto |
| 6,075,915 | A | 6/2000 | Koops et al. |
| 6,222,954 | B1 | 4/2001 | Riza |
| 6,301,420 | B1 | 10/2001 | Greenaway et al. |

(Continued)

FOREIGN PATENT DOCUMENTS

| | | |
|---|---|---|
| CN | 2663979 Y | 12/2004 |
| JP | 368815 A | 3/1991 |

(Continued)

OTHER PUBLICATIONS

Notice of Reasons for rejection for JP Application No. 2014-192655, dated Aug. 27, 2015, 4 pages.

(Continued)

*Primary Examiner* — Thomas A Hollweg
*Assistant Examiner* — Mary A El Shammaa
(74) *Attorney, Agent, or Firm* — Armstrong Teasdale LLP

(57) ABSTRACT

An optical sensor and method of manufacture are provided herein. The optical sensor includes an optical fiber comprising a terminating end surface, and a photonic crystal coupled to the terminating end surface of the optical fiber.

18 Claims, 4 Drawing Sheets

(56) References Cited

U.S. PATENT DOCUMENTS

| | | | |
|---|---|---|---|
| 6,691,007 | B2 | 2/2004 | Haugse et al. |
| 7,062,140 | B2 | 6/2006 | Bjarklev et al. |
| 7,289,221 | B2 | 10/2007 | Wang et al. |
| 7,359,587 | B2 | 4/2008 | Beausoleil et al. |
| 7,379,648 | B1 | 5/2008 | Brooks et al. |
| 2001/0054681 | A1 | 12/2001 | Hamada |
| 2003/0077058 | A1 | 4/2003 | Russell et al. |
| 2005/0053352 | A1 | 3/2005 | McKain et al. |
| 2005/0175274 | A1 | 8/2005 | Gunn, III et al. |
| 2005/0201660 | A1 | 9/2005 | Grot et al. |
| 2008/0129980 | A1 | 6/2008 | Dhawan et al. |
| 2009/0208163 | A1 | 8/2009 | Kilic et al. |
| 2009/0263079 | A1 | 10/2009 | Shapira et al. |

FOREIGN PATENT DOCUMENTS

| | | |
|---|---|---|
| JP | 2004117041 A | 4/2004 |
| JP | 2006524793 A | 11/2006 |
| JP | 2007232509 A | 9/2007 |
| JP | 2007293259 A | 11/2007 |
| WO | 2008086448 A2 | 7/2008 |

OTHER PUBLICATIONS

International Search Report and Written Opinion of PCT/US2010/050921; dated Sep. 21, 2011; 16 pages.

Jung, I. et al; Photonic Crystal Fiber Tip Sensor for Precision Temperature Sensing; Leos 2009 22nd Annual Meeting og the IEEE Lasers and Electro-Optics Society; Oct. 4-8, 2009; pp. 761-762; Belek-Antala, Turkey.

Jung, I. et al.; Monolithic Silicon Photonic Crystal Slab Fiber Tip Sensor; 2009 IEEE/Leos International Conference on Optical Mems and Nanophotonics. Opt Mems 2009; Aug. 17-20, 2009; pp. 19-20; Clearwater, FL.

Third Office Action for Chinese Application No. 201080048010.2, dated May 25, 2015, 25 pages.

Fifth Office Action for Chinese Application No. 201080048010.2, dated Apr. 20, 2016, 10 pages.

Canada Office Action for related application 2,772,453 dated Sep. 9, 2015; 4 pp.

JPO Office Action for related application 2014-192655 dated May 17, 2016; 3 pp.

Notification of the Decision of Rejection for Chinese Patent Application No. 201080048010.2, dated Nov. 2, 2016, 12 pages.

European Search Report for Application No. 10 779 077.6; dated Apr. 12, 2017, 5 pages.

OPTICAL SENSOR AND METHOD OF MANUFACTURE

CROSS REFERENCE TO RELATED APPLICATIONS

This application is a divisional of U.S. patent application Ser. No. 12/589,668, filed Oct. 26, 2009, which is incorporated herein by reference in its entirety.

BACKGROUND

Aerospace vehicles and systems are typically equipped with instruments that monitor the health of various systems by acquiring, exchanging and analyzing data, and the communication networks in such arrangements must be robust enough to withstand repetitive and potentially destructive forces and conditions, while transmitting and processing the data collected.

In recent years, there has been a trend to use optical apparatus in lieu of electrical or mechanical devices for the purpose of monitoring the health of such systems. Optical interrogation systems are integral components in health monitoring systems used in chemical, biological, temperature and pressure sensing environments. Optical sensing techniques are highly desirable for aerospace applications due to the lighter weight and EMI continuity, but to date such sensor systems have proven too costly or complicated to deploy.

Various solutions have been proposed and tried, including Fiber Bragg Grating (FBG) type sensor systems, fiber optic path sensing, piezoelectric transducers, comparative vacuum monitors, strain gauge based systems, ultrasonic systems, and visual indicators, but each has challenges.

Currently, while Fiber Bragg Grating devices are preferred in many fields of Structural Health Monitoring, such devices require careful modification of fiber optic cable to operate as well as complicated methods for determining wavelength shifts and other phenomena. Such systems also appear to be affected by temperature changes, requiring additional equipment to compensate.

Fiber optic path sensing is extremely attractive due to its simplicity (e.g., a loop of fiber), but the resulting system can become quite complex as monitoring for breakage or changes will typically require additional equipment such as Time Domain Reflectance equipment.

Piezoelectric devices tend to be quite expensive, due to the nature of the materials used in their construction. Such devices will also typically have features of other electrical based systems (susceptibility to EMI/Lightning) as well as the need for dual wire connections for each individual sensor. Further, such devices tend to be sensitive to certain frequencies, and may require a considerable amount of baseline data measurements in order to operate properly.

Comparative Vacuum Monitoring (CVM) makes use of very fine pressure cells and looks for pressure variations which signify cracks; this appears to make for a simple and affordable sensor design. However, CVM appears to require tubing and pressure systems in order to operate, and known CVM equipment appears to require the use of handheld systems in order to be used.

Strain Gauges are an older technology that looks at resistance changes. The sensors are quite simple, being in most cases just copper traces on a flexible substrate. Installing and reading such sensors accurately can be difficult however, and also has issues similar to the piezoelectric designs mentioned above.

Ultrasonic inspection is a technique currently being used, and requires installation of a field device run across structures and equipment in order to operate properly. Attempting to scale down such a system to an embedded type design would most likely result in a system very similar to a piezoelectric type system.

Visual inspection is the standard sensing method used at this time, and involves highly trained individuals inspecting and attempting to gauge failures of material, and estimating how long structures can last in service.

U.S. Pat. No. 6,691,007, issued to Haugse et al. on Feb. 10, 2004 and assigned to the assignee of the present disclosure, describes a system and method for monitoring conditions of a vehicle and generating a maintenance plan according to the monitored conditions. The patent discloses the use of conventional optical sensors, such as Fabry-Perot interferometric, long-period grating, and fiber Bragg grating sensors, none of which are small enough to permit miniaturization or diminished cost of the interrogator system.

A light-weight, miniaturized, and efficient optical interrogation apparatus is therefore needed to survey data from one or more optical sensors for the purpose of monitoring and reporting on the structural health of vehicle structures and systems.

BRIEF DESCRIPTION

In one aspect, an optical sensor is provided. The optical sensor includes an optical fiber comprising a terminating end surface, and a photonic crystal coupled to the terminating end surface of the optical fiber.

In another aspect, a method of manufacturing an optical sensor is provided. The method includes providing an optical fiber that includes a terminating end surface, and coupling a photonic crystal to the terminating end surface of the optical fiber.

Further aspects of the apparatus and the method of using the apparatus are disclosed herein. The features as discussed above, as well as other features and advantages of the present disclosure will be appreciated and understood by those skilled in the art from the following detailed description and drawings.

DETAILED DESCRIPTION

Embodiments of the present invention now will be described more fully hereinafter with reference to the accompanying drawing. However, many different embodiments are contemplated and the present disclosure should not be construed as limited to the embodiments set forth herein; rather, these embodiments are provided so that this disclosure will be thorough and complete and better convey the scope of the disclosure to those skilled in the art.

In its broadest sense, this disclosure presents a system for monitoring conditions in a vehicle and providing data representative of such conditions to a health management system residing in the vehicle. The system includes one or more optical sensors, and an optical interrogation apparatus located within the vehicle. The optical interrogation apparatus converts optical signals into electrical signals that can be used by the vehicle integrated health management system to monitor the status of the systems of the vehicle.

This disclosure further presents a structural health monitoring system that includes one or more optical sensors, an optical interrogation apparatus, and optically responsive infrastructure located between the sensor(s) and the interrogation apparatus. The health monitoring system is able to withstand extreme environments, and can be applied to chemical sensing, biological sensing, and temperature or pressure sensing.

Figure 1:
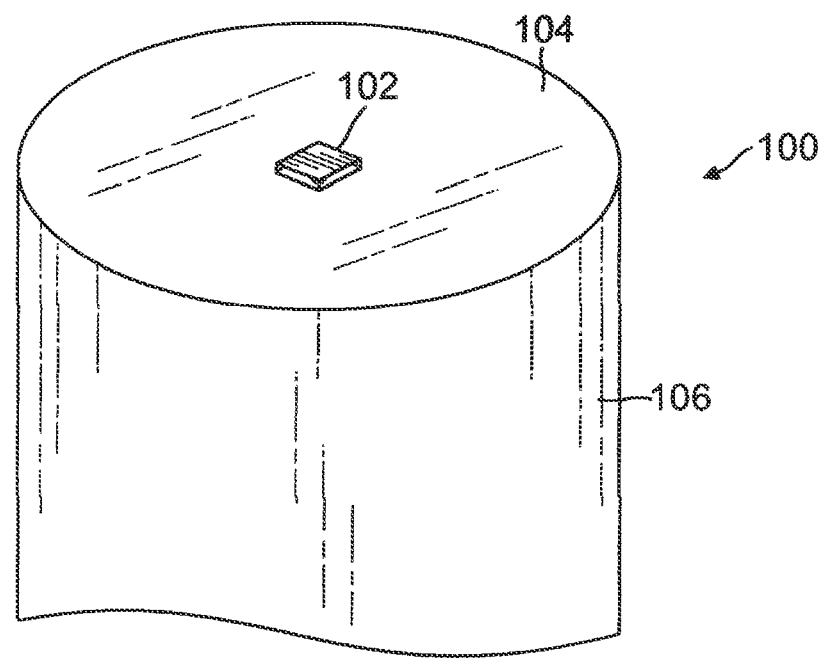
FIG. 1 is a perspective view of an optical sensor according to the present disclosure.

Referring to FIG. 1, an optical sensor 100 includes a photonic crystal 102 mounted on, and secured to, the end face 104 of a single mode optical fiber 106. The photonic crystal, in its simplest form, is made from a single layer of semiconductor material, but can include several layers of semiconductor material mounted on the end of the fiber strand 106. The sensor principle is based on detecting changes in the reflectivity spectrum of photonic crystals. The single layer photonic crystal has a sharp reflection resonance in the wavelength range that is being monitored. Preferably, the photonic crystal sensor is fabricated in a silicon foundry using standard fabrication processes, and will meet the requirements for size, interface characteristics, and robustness for operation in the harshest operating environments. Depending on the material construction, various effects can be monitored, as for example, pressure against the tip of the fiber. A more complicated buildup, for example applying a range of voltages to the photonic crystal to change reflectance properties, can allow a "smart" component to use the photonic crystal or wafer as a low powered communications device by modifying light reflectance that can be read by the optical interrogator. Another possible implementation would be to use the fiber as a side-scattering light guide, with a series of photonic crystal patches or a length of photonic crystal material monitored by a single fiber.

Photonic crystal sensors are also far less complicated to use and manufacture than the Fiber Bragg Grating sensors discussed earlier in this disclosure. Fiber Bragg Grating sensors are currently made by stripping the coating off of existing single mode fibers (from 125 micrometer glass fiber), "writing" the Bragg Grating into the fiber, and then recoating with a replacement material. Writing the grating into the fiber can be accomplished through the use of a laser and phase mask, as well as other methods. Selection of cladding replacement, writing process, and fiber composition can all have an effect on the final sensor performance. This is a complicated process to perform.

The Fiber Bragg Sensors can be highly sensitive which is a benefit, and they lend themselves to in-line construction along the length of a single fiber, capable of simultaneously reading data from 20 or more sensors. However, such devices operate by changing the wavelength of reflected light (short wavelength typically) across its length. This drives a lot of the complexity of the system into the interrogation equipment of the sensors, as it must be capable of reading extremely small changes (interference effects of all the fringe) in wavelength at very low amplitudes of reflected light. This, it appears, is a direct result of a great deal of variability introduced during fabrication which can complicate construction.

Additionally, Fiber Bragg Grating sensor operation requires a change along its length (e.g., stretching, bending, pressure, etc.). In some cases this is advantageous, but in most others, where a single point of interest needs to be monitored, it can be a liability. This also tends to make the sensors naturally sensitive to temperature changes (due to the flexing or stretching of the fiber sections) which must be compensated for.

In contrast, photonic crystals offer mass manufacturing capability, repeatability, and a highly controlled sensing area. These devices also act more as a pure reflector, with a greater return of incident light. Crystal lattices are fabricated using existing semiconductor techniques. These devices can then be cut out of wafers in much the same way as integrated circuits are. For a basic installation, a fiber end is polished using existing telecomm type equipment, and a lattice wafer is adhered to its surface. This element may be left bare, or it can be coated with a material that protects the crystal from destructive environmental conditions, depending on the intended application. The use of photonic crystals significantly reduces the weight and complexity of the components that make up the interrogator system of the present disclosure, thereby permitting miniaturization of the system.

Figure 2:
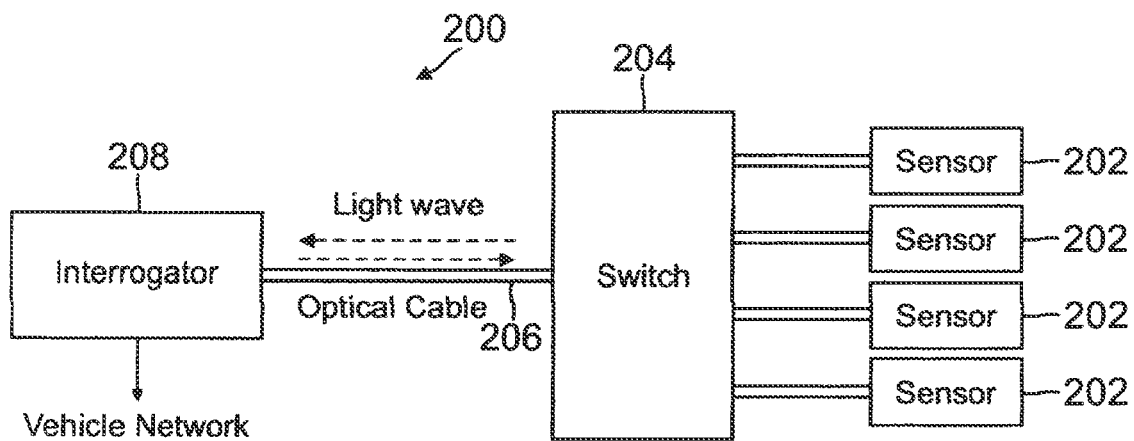
FIG. 2 is a schematic diagram that shows the structure of the optical interrogation system according to the present disclosure.

Referring to FIG. 2, the optical interrogation system 200 of the present disclosure is seen to include a plurality of optical sensors 202, an optical switch 204, optical cables 206, and an optical interrogator 208. Each sensor 202 comprises the fiber-plus-photonic-crystal (FPPC) structure 100 described above.

The optical switch 204 may be an integrated, all-solid-state device that is small, lightweight, and capable of withstanding a wide range of vibrations. This device, which may include one or more microelectromechanical system switches (MEMS), is reliable in harsh environments, is failure tolerant, and is easily serviceable. The optical network shown in FIG. 2 integrates fast-tunable semiconductor lasers with optical passive wavelength routers, such as waveguide routers. The lasers enable the use of high capacity, low power consumption optical packet switches and a light weight interrogator.

The optical interrogator 208, which converts optical signals to electrical signals that are used by the vehicle health management system to monitor the status of the system sensors located at remote locations in the vehicle, is similar to but replaces the conventionally used Fiber Bragg Grating sensor systems.

Figure 3:
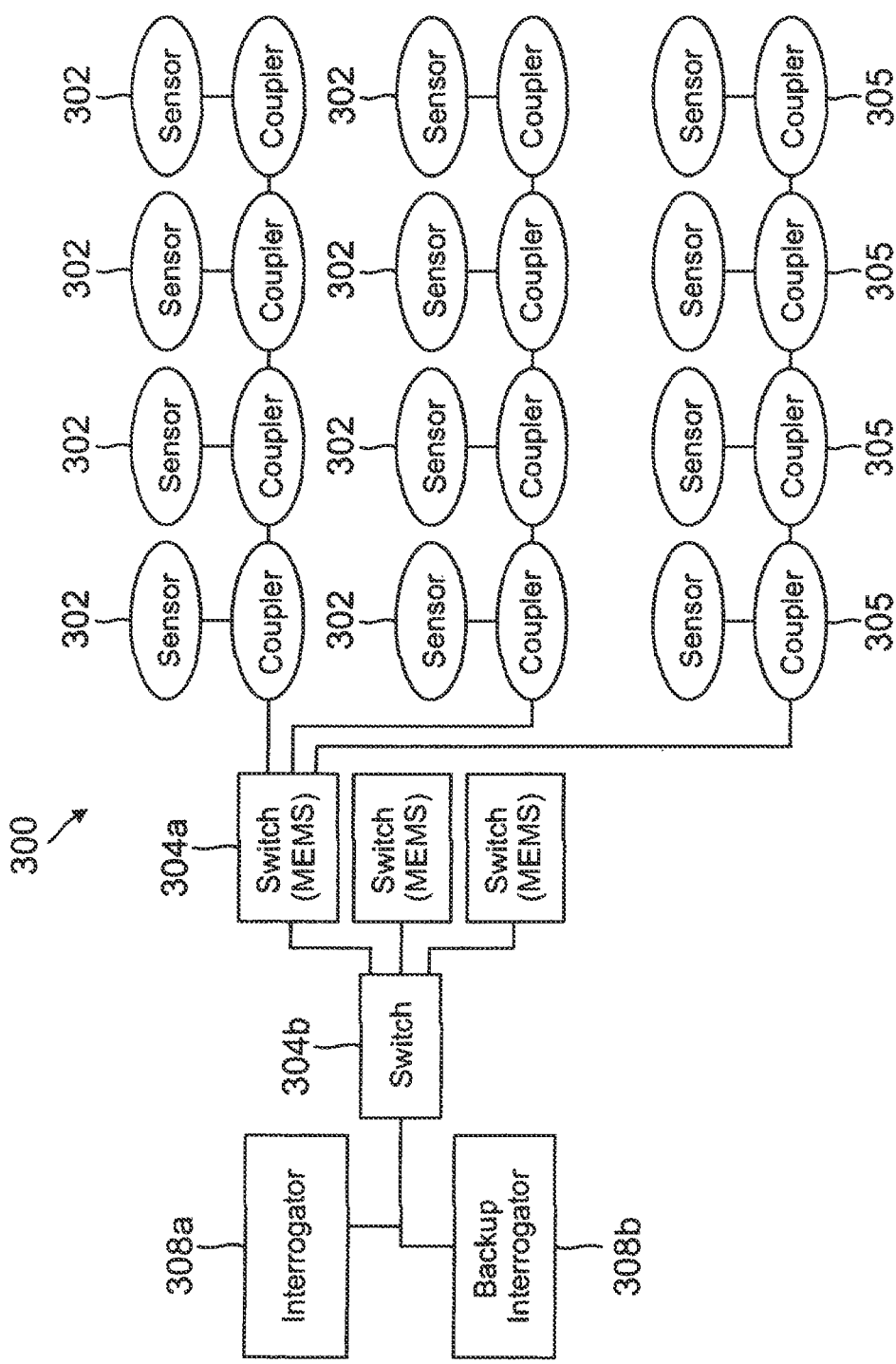
FIG. 3 is a schematic diagram showing a failure tolerant optical switching system according to the present disclosure.

FIG. 3 depicts another system 300 according to the present disclosure emphasizing a redundant architecture that offers failure tolerance to the vehicle network. A plurality of optical sensors 302 of the type shown in FIG. 1 are each connected to a MEMS switch 304a through a coupler 305. The MEMS switches 304a provide connections to a back-up switch 304b, so that the on-board optical network can operate with minimum delay in the case of failure of the fiber-optic cables or the wave guide grating routers. The MEMS switches 304a are small, wavelength-insensitive, and optically transparent, and thus are simple to install and operate. Further, their switching time is on the order of tens of microseconds, which is sufficiently fast for recovery of most functions given the proper redundancy management implementation. The system further includes a primary interrogator 308a and a backup interrogator 308b.

Figure 4:
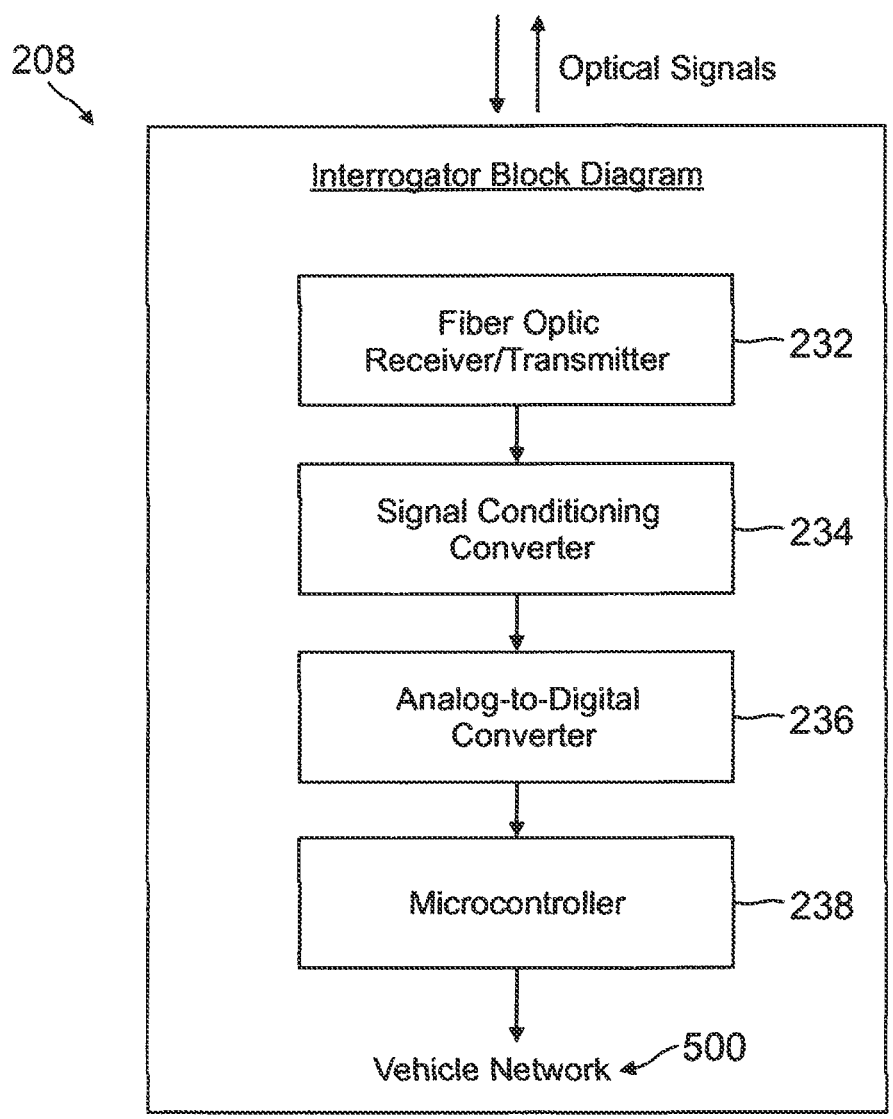
FIG. 4 is a block diagram of the optical interrogator according to the present disclosures.

FIG. 4 is a block diagram illustrating the components that make up the optical interrogator 208 of the present disclosure. Interrogator 208, which provides an interface between the optical sensors and the control and data acquisition systems of the vehicle network 500, includes a fiber optic receiver/transmitter 232, a signal conditioning converter 234, an analog to digital converter 236, and a microcontroller 238. The fiber optic receiver 232 converts the light intensity from an optical fiber into an electrical signal, which is amplified and passed to a filter circuit that conditions the signal for input to the analog-to-digital converter 236. From there, the digitized signal is sent for analysis to the microcontroller 238, the latter monitoring the signal to determine if it falls below a specified threshold. If such is determined, the microcontroller sends a warning signal to the vehicle network 500.

Figure 5:
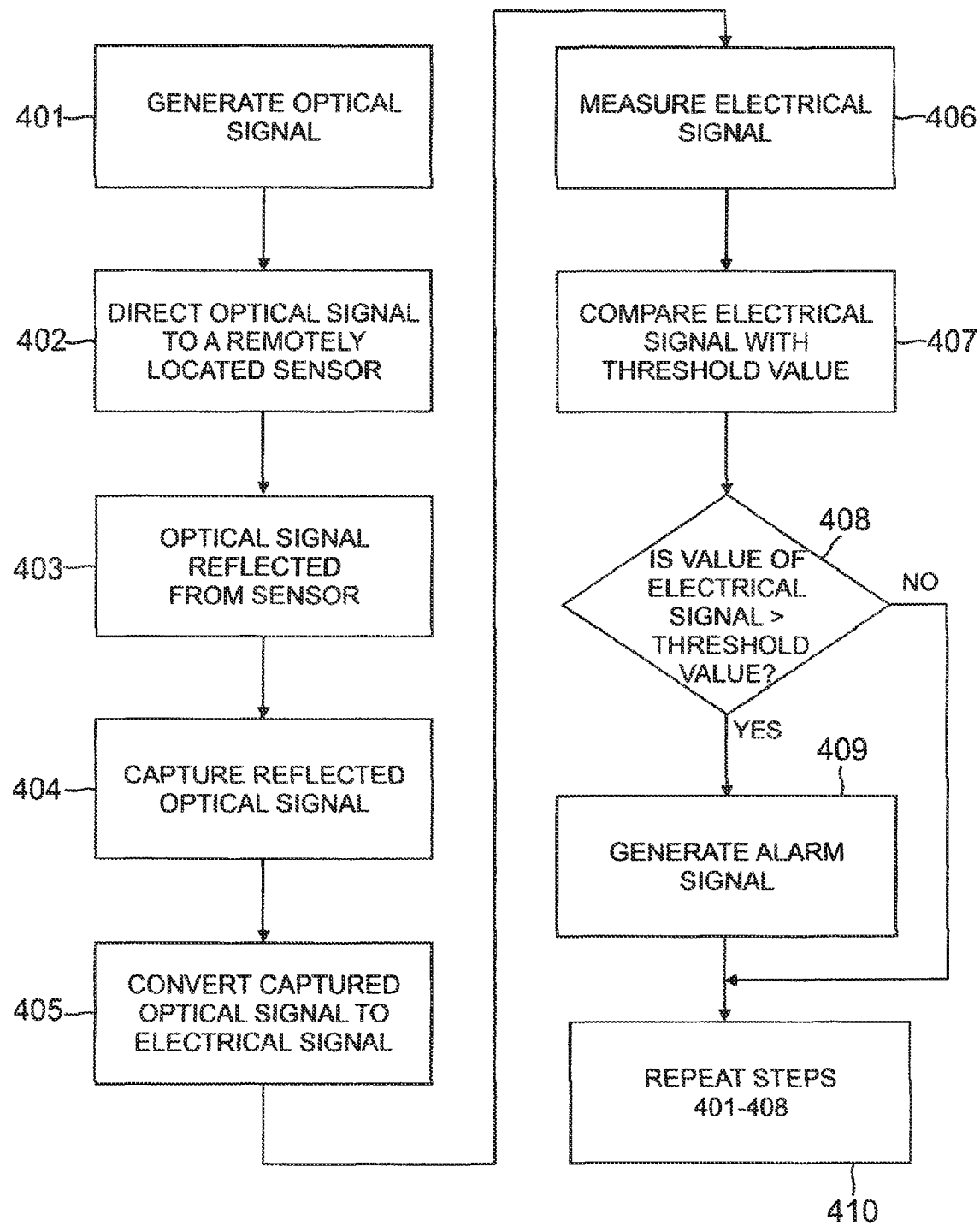
FIG. 5 is a block diagram illustrating steps of a method of monitoring conditions of a vehicle using an optical sensor, as has been described herein.

FIG. 5 is a block diagram showing steps of a method for monitoring the structural health of a vehicle according to the present disclosure. In block 401, a first step entails generating an optical signal, as for example, by a laser or LED. Next, as shown in block 402, the optical signal is directed at a remotely located optical sensor in the vehicle. The sensor includes a fiber optic cable with a photonic crystal mounted to an end surface of the cable, as described above in connection with FIG. 1. In block 403, the optical signal is reflected from the sensor, and is returned and captured by optical signal receiving apparatus, as shown in block 404. In the step represented by block 405, the optical signal is converted to an electrical signal, and any signal conditioning, such as filtering and/or amplifying the signal is then carried out. In the step represented by block 406, the attributes) of interest of the electrical signal is measured. Attributes of the signal which might be of interest include its amplitude, its frequency, its wavelength, etc. In the step shown in block 407, the measured attribute(s) of the electrical signal is/are compared to a pre-selected threshold value, which may represent an acceptable upper limit value of the measured attribute. Next, as shown in block 408, the method executes a decision as to whether the value of the electrical signal attribute exceeds the respective threshold values. If the value of the electrical signal attribute exceeds the threshold value, an alarm signal is generated (at block 409) and the method proceeds to block 410 where the steps of blocks 401-408 may be repeated in accordance with the requirements of the monitoring process schedule. On the other hand, if the value of the electrical signal attribute does not exceed the threshold value, then the method proceeds directly to block 410 where steps 401-408 are repeated according to the monitoring process schedule. It is to be understood that the monitoring process schedule might call for a single interrogation of the optical sensors at user predetermined intervals, continuous interrogation, repeated sets of interrogation at user selected intervals, or any combination of interrogations and intervals. Any of the attributes of the electrical signal that may be of interest may be measured and evaluated, and compared against a corresponding threshold value, preferably determined and established before installation in the vehicle.

An optical interrogation system according to the present disclosure is light-weight and miniaturized, and can withstand extreme environments. The system can be applied to chemical sensing, bio sensing, and temperature, pressure sensing. Also, it can be embedded in an aircraft fuselage and where health monitoring is desired. The sensor interrogation system of this disclosure penetrates into the most demanding environments, e.g. engines and weight-bearing structures; their packaging and electronic integration are designed to tolerate extremes of temperature, mechanical vibration, corrosive materials and electromagnetic interference, while retaining a small overall volume and non-intrusive operation so as to not adversely affect operation of the systems that are monitored.

The apparatus of this disclosure will allow for the addition of switch type devices in order to increase the reuse of the interrogator hardware. Current state of the art Fiber Bragg Grate Sensor systems appear to focus on the use of splitters and couplers almost exclusively. While this arrangement can provide extremely fast access to sensor data, as the system is essentially connected to everything at once, it appears to complicate the interrogation device design as all of the simultaneous reflections must be "decoded" at once. The Fiber Bragg Grate sensors also appear to only be capable of light modification in a very narrow spectral band, which requires additional sensitivity in the interrogator.

The photonic crystal approach permits switching devices to operate in the micro-, to milli-, second range dependent on size. In cases such as structural health monitoring, an aircraft may in fact not need to have its sensing network activated except in certain conditions where the system must be polled every few seconds, minutes, or even hours. Taking advantage of this, it should be possible to reduce the complexity, cost and size of the interrogator system while also increasing redundancy that may be built into the system.

For the illumination source, laser and tunable laser systems currently appear to be the best interrogation apparatus. CCD type equipment may be used as the sensing devices; however, filtered light sensors in arrays may also be used. While this apparatus is already used for the Fiber Bragg Grate Sensors, the use of photonic crystal based materials makes design of the system far easier, and could enable the use of lower quality light sources, such as LEDs, which may also be of use in this sensor system as more light energy will be reflected and there is less need to worry about delicate wavelength shifts.

Additionally, this sensing approach may lend itself to even lower cost sensing solutions. For example, it may in fact be possible to make use of this approach with much cheaper plastic fiber cable, standard light emitting diodes for light sources, and cheaper light sensors. In this way the same sensing system can be adapted for low cost use in areas such as panel switching, simple proximity sensing (doors), and low quality pressure type applications (occupancy weight sensing systems such as are used in automobiles) and other applications where a low weight, low cost, and yet EMI immune system would be of benefit. Such scalability between low reliability-need systems and high reliability systems appears attractive from a research standpoint.

While the disclosure has been made with reference to a preferred embodiment, it will be understood by those skilled in the art that various changes may be made and equivalents may be substituted for elements thereof without departing from the scope of this disclosure.

What is claimed is:
1. An optical sensor, comprising:
an optical fiber comprising a core having a terminating end surface, said core having a first width; and only one photonic crystal attached directly against said terminating end surface of said core of said optical fiber, said photonic crystal having a second width, wherein the second width is less than the first width.
2. The optical sensor of claim 1, wherein said terminating end surface comprises a polished terminating end surface, wherein said photonic crystal is secured to said polished terminating end surface.

3. The optical sensor of claim 1, wherein said photonic crystal is coated with a material that protects said photonic crystal from destructive environmental influences.

4. The optical sensor of claim 1, wherein said photonic crystal is configured to receive a range of applied voltages that alter reflectance properties of said photonic crystal.

5. The optical sensor of claim 4, wherein the reflectance properties altered by the range of applied voltages indicate a pressure against said terminating end surface of said optical fiber.

6. The optical sensor of claim 4, wherein said photonic crystal modifies light reflectance that is readable by an optical interrogator to act as a low-power communications device.

7. The optical sensor of claim 4, wherein said optical fiber is applied as a side-scattering light guide and a length of photonic crystal material is monitored by a single fiber optic strand.

8. The optical sensor of claim 1, wherein said optical fiber comprises a single mode optical fiber.

9. The optical sensor of claim 1, wherein said optical fiber comprises a fiber optic strand, wherein said photonic crystal is attached directly against a terminating end surface of said fiber optic strand.

10. The optical sensor of claim 1, wherein said photonic crystal comprises a crystal lattice semiconductor cut into a wafer.

11. A method of manufacturing an optical sensor comprising:

providing an optical fiber that includes a core having a terminating end surface, the core having a first width; and attaching only one photonic crystal directly against the terminating end surface of the optical fiber, the photonic crystal having a second width, wherein the second width is less than the first width.

12. The method of claim 11, further comprising
polishing the terminating end surface, and
securing the photonic crystal to the polished terminating end surface.

13. The method of claim 11, further comprising coating the photonic crystal with a material that protects the photonic crystal from destructive environmental influences.

14. The method of claim 11, wherein providing the optical fiber comprises providing a single mode optical fiber.

15. The method of claim 11, wherein coupling the photonic crystal comprises attaching the photonic crystal directly against the terminating end surface.

16. The method of claim 11, wherein providing the optical fiber comprises providing a fiber optic strand.

17. The method of claim 16, further comprising coupling the photonic crystal to a terminating end surface of the fiber optic strand.

18. The method of claim 11, further comprising:
fabricating a crystal lattice semiconductor; and
cutting the crystal lattice semiconductor into a wafer.

* * * * *